United States Patent [19]
Blugerman et al.

[11] Patent Number: 5,447,493
[45] Date of Patent: Sep. 5, 1995

[54] TUMESCENT LIPOPLASTIC APPARATUS

[75] Inventors: Guillermo S. Blugerman; Diego E. Schavelzon, both of Buenos Aires, Argentina

[73] Assignee: Very Inventive Physicians, Inc., Tucson, Ariz.

[21] Appl. No.: 179,747

[22] Filed: Jan. 10, 1994

[51] Int. Cl.$^6$ ............................................. A61M 1/10
[52] U.S. Cl. ...................................... 604/35; 604/22; 604/902
[58] Field of Search ........................ 604/19, 22, 27, 35, 604/902

[56] References Cited

U.S. PATENT DOCUMENTS

| | | | |
|---|---|---|---|
| 4,696,669 | 9/1987 | Menhusen | 604/34 |
| 4,863,439 | 9/1989 | Sanderson | 604/264 |
| 5,236,414 | 8/1993 | Takasu | 604/22 |
| 5,242,386 | 9/1993 | Holzer | 604/22 |
| 5,244,458 | 9/1993 | Takasu | 604/22 |

*Primary Examiner*—Corrine Maglione
*Attorney, Agent, or Firm*—Ogram & Teplitz

[57] ABSTRACT

An improved medical tool which combines tumescent anesthetic solution with lipoplastic. Using a peristaltic pump and a cannula, the surgeon directs the tumescent solution into the area of concern. The tumescent solution provides both a local anesthetic as well as a vasoconstrictor. The solution eliminates the need for a general anesthetic, thus eliminating problems associated therewith, and the solution causes the blood vessels to constrict, reducing the amount of blood loss during the procedure. Once the solution has had an opportunity to perform its function, the surgeon reverses the direction of the peristaltic pump and removes the fat and tissue through the same cannula used for the tumescent portion of the operation. Since the suction process is performed by the peristaltic pump (as opposed to manually by the surgeon), the cannula is reduced in size to a highly versatile and tactile instrument providing highly improved results.

19 Claims, 3 Drawing Sheets

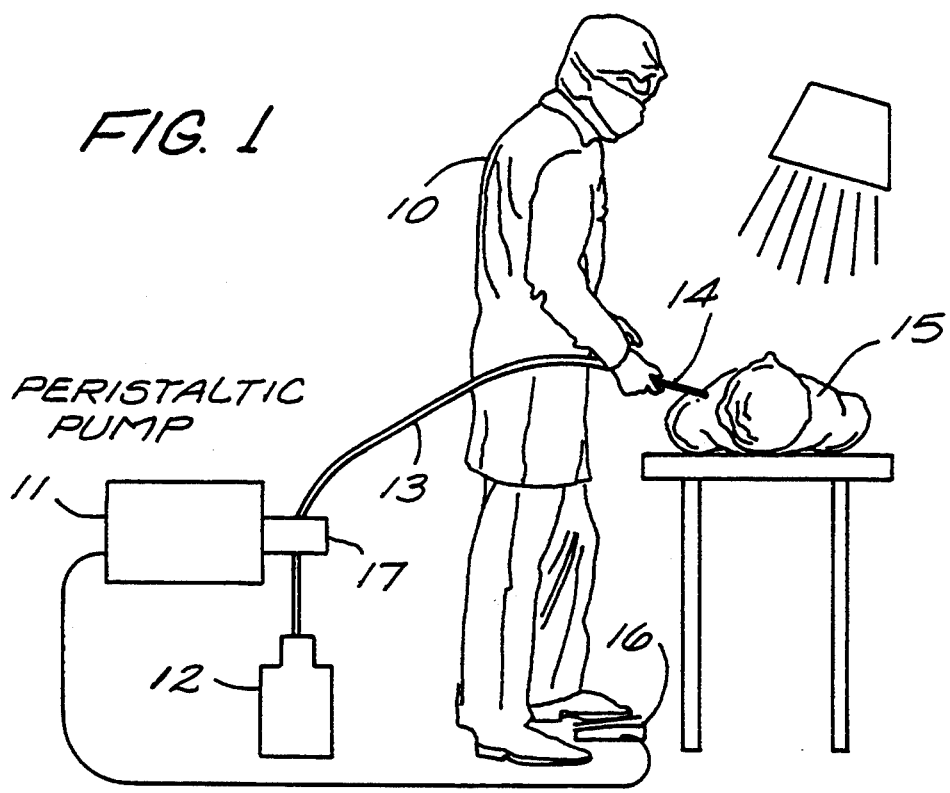
FIG. 1
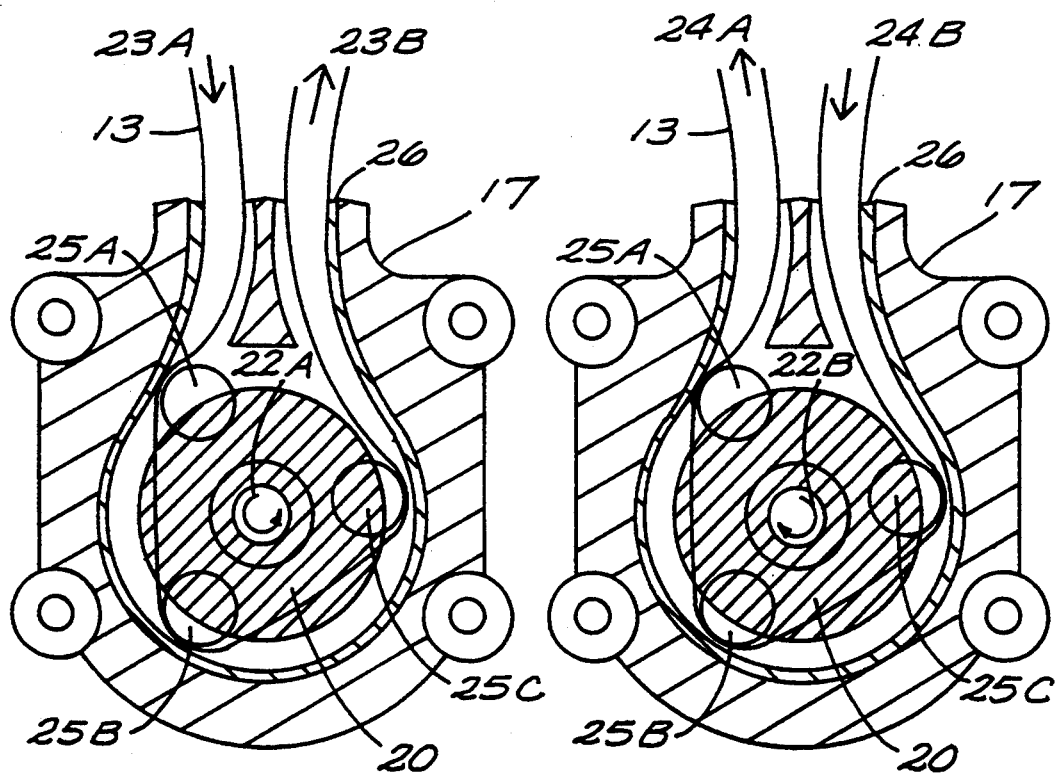
FIG. 2A
FIG. 2B

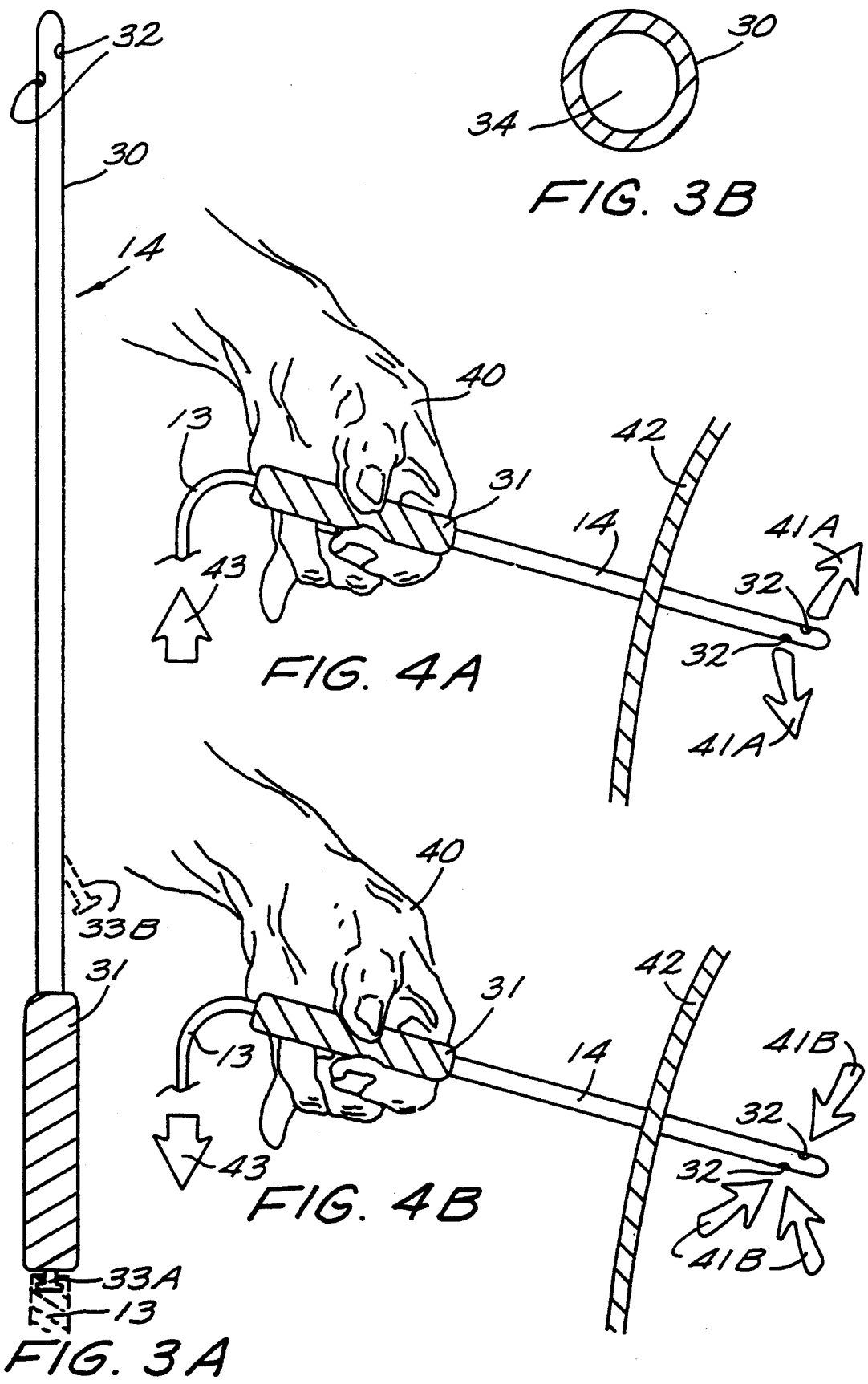

TUMESCENT LIPOPLASTIC APPARATUS

BACKGROUND OF THE INVENTION

This invention relates generally to surgical instruments and techniques and more particularly to instruments and techniques used in the removal of tissue and fat from a patient.

In the area of cosmetic or aesthetic surgery, body contouring is accomplished through a variety of ways including liposuction in which body fat and tissue are removed through the use of high vacuum pressure.

One of the earliest discussions of liposuction was made by Dr. Y. G. Illouz in 1983 (Illouz, Y. G., "Body Contouring by Lipolysis: A 5-Year Experience with over 3000 cases", Plast. Reconstr. Surg. 72; 591, 1983) in which some three thousand cases were discussed. This technique has changed little over the years and is commonly referred to as the "wet" method. A mixture of isotonic saline and epinephrine or vasopressin is used in differing dilutions. A general aesthetic is given. Using tunnels or strokes, the mixture is inserted into the patient in the area of interest. Using any of a wide range of cannulas, the tissue or fat is then withdrawn.

The withdrawal of the fat is usually accomplished through one of two methods.

In the first method, a cannula is affixed to end of a large syringe. The cannula is inserted into the patient such that the tip of cannula is in the area of interest and the surgeon creates a suction by withdrawing the plunger of the syringe. When the syringe is filled, the cannula is withdrawn from the patient and the contents of the syringe are discharged into a receptacle. The surgeon continues with this procedure (aspiration/discharge/aspiration/discharge/ . . . ) until the desired contouring is accomplished.

In this method though, because of the syringe's own capacity limitations, the process requires the repeatedly re-entry until the proper amount of tissue and fat is removed. Enlargement of the syringe to accommodate more volume is not feasible because, even at the present size, the syringe is so large and bulky that it is difficult for the surgeon to properly manipulate the end of the cannula.

Further, cosmetic surgery surgeons are quickly recognizing that a body's own fat may be used elsewhere on the body to provide contouring there. One such location where body fat has been used is near the corrugator supercilia muscle to correct for age lines in the face.

Because the fat/tissue aspirated by the syringe is discharged in an air environment, there is a danger that it can become contaminated making it unsuitable for re-injection into the body. The mere exposure of fat to air changes its physical characteristics making it less suitable for other body contouring applications.

In the second method, a suction pump is used to withdraw the fat/tissue. Again a cannula is used to direct the point of vacuum to a desired location. The fat/tissue is pumped from the patient using a conventional surgical pump. The aspirated materials pass through the pump and then into a repository.

Because of the intermediate step of the pump, and contacts therewith, the fat so collected is still suspect of contamination and is used only in extreme cases.

Additionally, because the cannula picks up air either due to gas entering the body cavity or during withdrawal of the cannula from the body, the suction force varies dramatically as the pump deals with the highly compressible air. This makes it more difficult for the surgeon to obtain consistent results.

Probably the most persuasive problems associated with either method is the excessive bleeding associated with the procedure and aesthetic sequelae (Erik Dillerud, "Suction Lipoplasty: A Report on Complications, Undesired Results, and Patient Satisfaction Based on 3511 Procedures", Plast. Reconstr. Surg., 88, 239, 1991).

It is quite common to withdraw as much blood as fat/tissue. This dramatic withdrawal of blood is not critical where a low amount of fat is removed, but, when a larger volume of fat/tissue is needed to be removed, complications result and recuperation time is extended and in almost all situations, supplemental blood is added to the patient, posing other dangers.

The aesthetic sequelae which has been experienced encompasses those well known with other types of surgery including: cardiac arrest, anaphylactic reaction, and respiratory arrest.

To increase the safety of the procedure, Klein has introduced the use of tumescent techniques using a local anesthesia (Klein, J. A., "Tumescent Technique for Local Anesthesia Improves Safety in Large-Volume Liposuction", Plast. Reconstr. Surg., 92, 1085, 1993). The tumescent technique involves the infiltration of a solution of lidocaine, epinephrine, sodium bicarbonate, and triamcinolone into the subcutaneous fat. Infusion is made through the use of a peristaltic pump. The tumescent solution reduces bleeding and eliminates the need for general anesthetics. The actual liposuction was conducted in the same manner as discussed before and hence had all of the limitations associated therewith.

Perhaps the largest problem associated with any of these methods is the risk to the health-care worker from aerial contamination and from the required multiple handling of the syringe. The syringe is passed from one party to another for aspiration of the fat from the patient, to expulsion into a container, and back for aspiration. This handling increases the potential of a puncture to one of the health care worker.

Additionally, in all of these procedures, a team is required for the surgery. This team must work together in withdrawing the fat and the handling of the instruments. As more people enter into the operation, the time required for the operation increases resulting in more trauma to the patient.

It is clear that the lipoplastic procedures and equipment of the current art creates certain dangers to the patient, and inhibits the surgeon's ability to perform the operation. Improvement of these procedures and equipment is needed.

SUMMARY OF THE INVENTION

The invention is an improved medical tool and procedure, which combines tumescent anesthetic solution with lipoplastic. Using a peristaltic pump and a cannula, the surgeon directs the tumescent solution into the area of concern. The tumescent solution provides both a local anesthetic as well as a vasoconstrictor. The solution eliminates the need for a general anesthetic, thus eliminating problems associated therewith; and, the solution causes the blood vessels to constrict, reducing the amount of blood loss during the procedure.

The tumescent solution is preferably administered through the cannula, although in one embodiment of the invention, a needle is used for the injection of the tumescent solution. The preferred size of this needle is a 2 gauge spinal needle. In either case, cannula or needle, the instrument acts as a conduit for the injection and aspiration activities.

Should a needle and cannula be used, the air pocket inside the cannula is preferably removed through the pumping of a sterile solution into the cavity of the cannula. This sterile solution is usually a saline solution and eliminates the delay in suction power once the aspiration step begins.

Once the solution has had an opportunity to perform its function (usually in a matter of seconds), the surgeon reverses the direction of the peristaltic pump and removes fat and tissue through the same cannula used for the tumescent portion of the operation.

Since the suction process is performed by the peristaltic pump (as opposed to the syringe of the prior art), the cannula is reduced in size to provide a highly versatile and tactile instrument permitting improved results.

In some applications, several cannulas are used during the operation so that the desired results are obtained.

The tumescent technique for the application of local anesthesia is well known and uses a variety of medicated solutions. The preferred solution uses 1000 milliliters of normal saline with 2% lidocaine, 30 ml. (600 mg) of epinephrine, and one mole (12.5 ml. or 12.5 mg.) of sodium bicarbonate. These additives are commercially available. To improve the lidocaine action and to reduce infiltration suffering, the preferred method is to apply the tumescent solution at body temperature. Heating of the solution is typically done through the use of a microwave oven although other heating techniques well known in the art, are also acceptable. In some applications, the tumescent solution is not heated.

Although the tumescent solution ideally eliminates the need for a general anesthetic, there are still times in which a general anesthetic is required and is used in conjunction with the tumescent solution. In this case, the tumescent solution provides for a vastly improved recuperation rate and comfort level for the patient.

Other possible means for injection of the tumescent solution include the traditional method of syringe injection and the in-bag solution in which the tumescent solution is forced into the patient from a flexible bag being squeezed either manually or with the assist of a blood pressure cusp.

Using a cannula, which draws upon the solution via a peristaltic pump, the tumescent solution is injected into the patient at the site of interest. The amount of solution which is injected is controlled by the surgeon through adjustment of the headstock (rotational direction and speed) of the peristaltic pump and by foot control of the peristaltic pump's on/off operation.

By reversing the flow from the peristaltic pump (reversing the headstock's rotating direction), the surgeon aspirates fat, tissue, and some of the tumescent solution from the patient. The aspirated material is pumped back into the reservoir from which the tumescent solution was originally stored and drawn.

The use of a peristaltic pump is preferred for this structure but other arrangements exist which are also acceptable. One such arrangement is the use of two pumps, one for injection and one for aspiration, which permits the surgeon to simply activate the proper pump. Another approach uses a single direction peristaltic pump. Reversal of this arrangement requires merely the removal of the flexible tubing from the peristaltic pump and its replacement in an opposite direction.

Note that the surgeon is not manually providing the vacuum for the liposuction portion of the procedure, rather, the peristaltic pump relieves the surgeon of this duty permitting a single hand of the surgeon to manipulate the cannula. This significantly eases the burden on the surgeon.

Similarly, the cannula used in the procedure can be reduced in size and complexity since, for all intents and purposes, the cannula is merely a tube or extension of the tubing. In the preferred embodiment, the cannula is reduced to a device having a handle less than twenty millimeters in diameter.

The fat and tissue which is drawn from the patient is kept within a sealed environment and is collected in the reservoir. Should this fat or tissue be needed for body contouring elsewhere on the patient, contamination has been reduced to minimum.

For re-injection, the surgeon merely provides an incision in the area of question and the peristaltic pump is put in a position to "pump" back to the patient. The surgeon, using the same cannula, is able to re-inject the patient's own fat with extreme precision and safety.

Since the peristaltic pump is dealing only with liquid or fat/tissue, the pump is able to provide an essentially instantaneous high vacuum immediately after injecting the tumescent solution into the patient. No air is permitted into the system which would degrade or delay the vacuum potential. This elimination of the latency of the vacuum is critical as the surgeon is now able to deal with a consistent operation of the system.

Using the instrument as described above, the surgical procedure involved is extremely simplified over the prior art. The preferred steps for the body contouring are:

Step 1: Apply an incision to gain access to the tissue or fat which is to be removed for the body contouring;

Step 2: Insert the cannula (or needle) through the incision and maneuver the tip of cannula to lie in the area to be contoured;

Step 3: Via the cannula (or needle), apply the tumescent solution to the site;

Step 4: Reverse the pumping direction of the peristaltic pump;

Step 5: Via the cannula, withdraw tissue and fat from the site, depositing the aspirated material back into the bag acting as the source of the tumescent solution.

Should the surgeon be using the aspirated fat tissue to correct another body contour anomaly, further steps are taken:

Step 6: Apply a second incision near the second anomaly;

Step 7: Insert the cannula near the second anomaly;

Step 8: Adjust the peristaltic pump to inject;

Step 9: Inject aspirated fat from the reservoir into the site.

In some situations, it is preferred to let the aspirated material to stratify before going to the steps for correcting a second anomaly requiring the injection of the patient's fat. Several techniques are well known to those of ordinary skill in the art for this procedure.

The invention together with various embodiments thereof will be more fully explained by the drawings and the following descriptions.

DRAWINGS IN BRIEF

FIG. 1 pictorially illustrates the invention in use in an operating room.

FIGS. 2A and 2B are cross sectional views of the headstock of the peristaltic pump and illustrate the reversibility of the pump.

FIG. 3A and FIG. 3B are side view and a cross sectional view of the preferred cannula used in the present invention.

FIG. 4A and 4B pictorially show use of the cannula and the resulting delicate grip required from the surgeon.

Figure 5A:
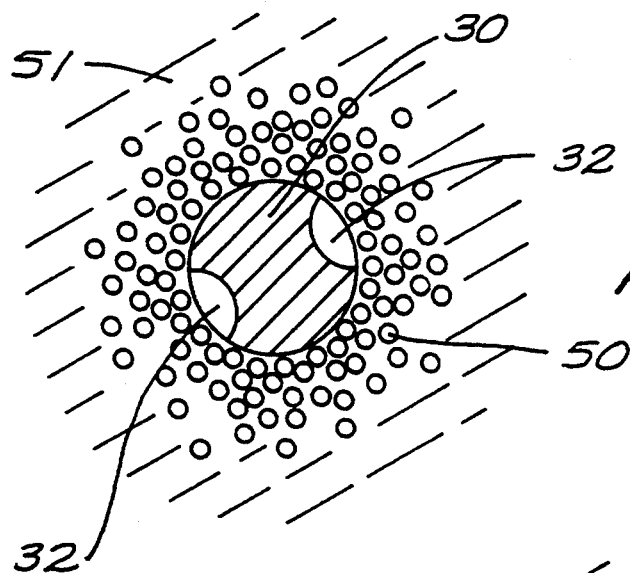
Figure 5B:
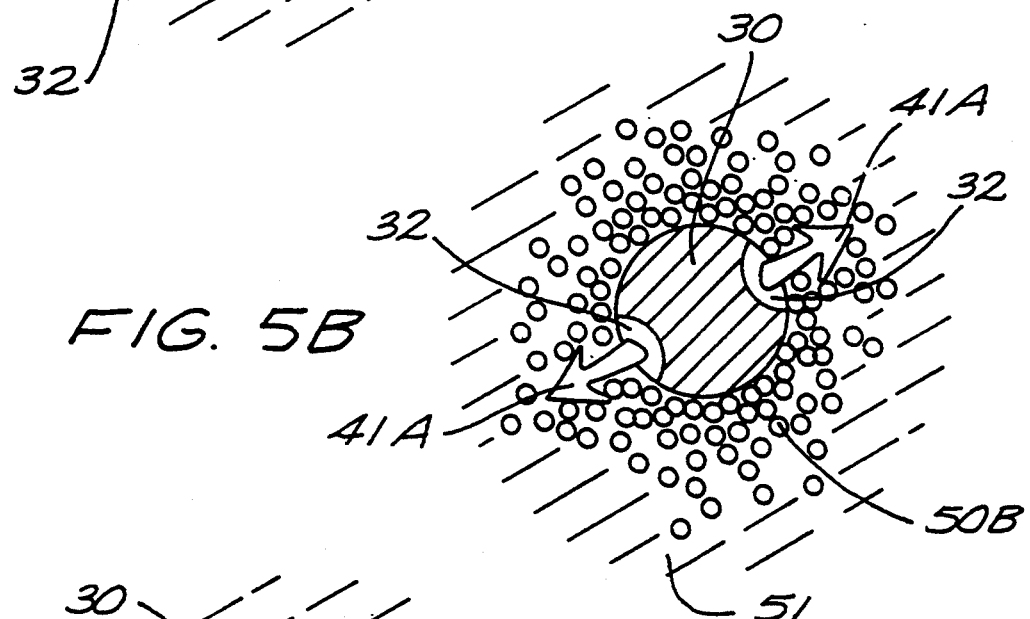
Figure 5C:
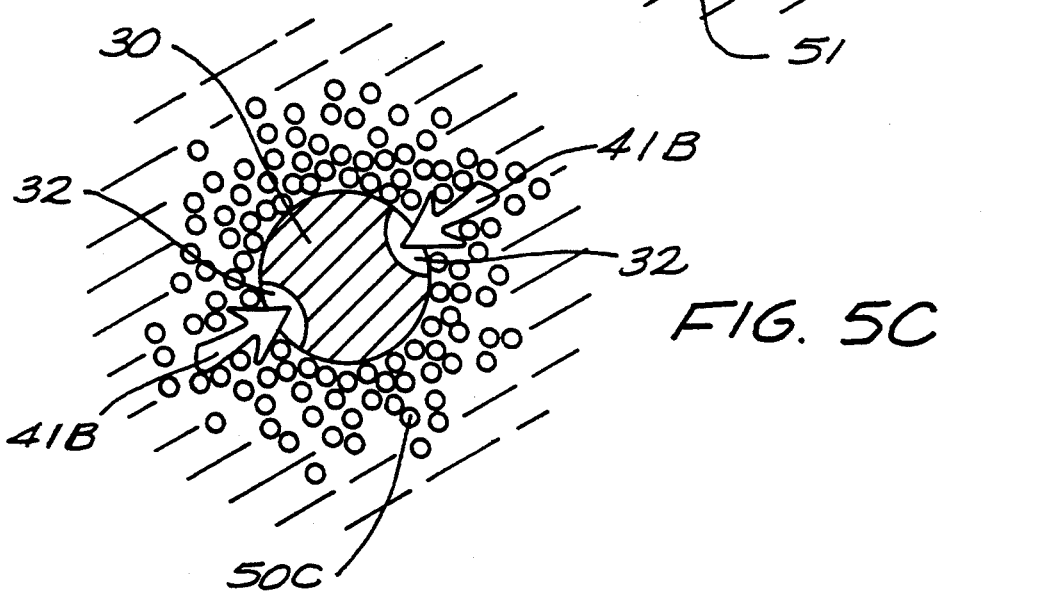

FIGS. 5A, 5B, and 5C pictorially illustrate the injection and aspiration in a patient of the present invention.

DRAWINGS IN DETAIL

FIG. 1 pictorially illustrates the invention in use in an operating room.

The surgical tool is made up of cannula 14, reservoir 12, flexible tubing 13 connecting cannula 14 with reservoir 12, and peristaltic pump 11. Peristaltic pump 11, via head stock 17, causes the liquid within tubing 13 to flow in either direction.

A sealing member which attaches to the skin is also preferably used to seal the edges of the cannula once insertion into the patient is made. This sealing member, not shown, attaches around the incision and provides for a "rubber-like" seal with the cannula to prevent liquids from escaping from the patient and from air entering the patient.

The preferred peristaltic pump 11 has a headstock 17 which is made of three rotating rollers which compress tubing 13 against a hard wall to cause suction at one side and ejection in the other.

A knob and other controls permit the surgical team to regulate both the rollers' rotational speed and direction, thereby controlling the flow rate and direction. A hand or foot control 16 is used by the surgeon to activate the peristaltic pump. Preferably the peristaltic pump stops substantially instantaneously so that the surgeon has optimal control.

Although this embodiment uses a peristaltic pump, vacuum pumps are also usable in this context although they have some practical drawbacks. The advantages enjoyed by the peristaltic pump are: low maintenance; no post-operative cleaning requirements; light weight and easy to carry; low noise level; no room pollution since oil is not used; fast priming; and, in this context, two functions in only one unit.

Tubing 13 is any of those well known in the art. In the preferred embodiment, tubing 13 is made of transparent polyvinyl chloride (PVC). Being transparent PVC, the flow of materials may be monitored by the surgeon.

Tubing 13 is kept sterile prior to use by being packaged in a double pouch and is a disposable item. Mechanisms, to attach tubing 13 to cannula 14, are any of numerous mechanisms including a plastic truncated cone or a Luer-Lok coupling. Those of ordinary skill in the art readily recognize various other coupling mechanisms which could be used in this context.

The middle part of the tubing 13, that which contact headstock 17, is made of a softer elastic material which permits the easy and efficient rotation of headstock 17. This center portion is made from a variety of materials including: Norprene, silicone, Tygon, Vitton, Pharmed, or C-Flex.

Reservoir 12 is preferably a plastic bag commonly found having capacities of 250 cc. to 2000 cc, or more. For some applications, 2000 cc to 3000 cc. of tumescent solution is injected into the patient.

Due to the use of tubing 13 and reservoir 12, the materials withdrawn from the patient are kept completely enclosed which significantly reduces the risk of aerosol mist and contamination to either the operating room or the health-care workers.

In one embodiment of the invention, a second reservoir used, not shown, which has a safety valve for venting from the primary reservoir should the primary reservoir become filled to capacity. This over-flow capability eliminates the possibility of the primary reservoir rupturing during the operation.

In the preferred embodiment, the reservoir is graduated permitting:

1. the surgeon to know exactly how much material was aspirated from every region (different bags for different regions);
2. the re-injection of aspirated fat with the assurance that the fat has not been exposed to the air;
3. the collected material to be sent to the laboratory without any repackaging (i.e. for culture and pathological tests);
4. aspirated tissues and auto-collagen to be used further;
5. processing of the fat for filler in inflatable prosthesis;
6. separation of blood elements for auto-transfusion; and,
7. easier disposal of pathological remains without the requirement of personnel handling the remains.

Because of the enhanced capability that the combination of reservoir 12/ peristaltic pump 11/ and tubing 13 provide, the physical requirements of cannula 14 are dramatically changed permitting cannula 14 to become a delicate instrument giving the surgeon heretofore unavailable sensitivity in this type of surgery and single-hand operation of the cannula.

Should cannula 14 be withdrawn from the patient, permitting air into the cannula's cavity, the cavity should be refilled with the tumescent solution by merely adjusting the pump to infuse solution into the cavity.

Of significance is the replacement of the bulky handle used in the prior art with a delicate handle which is controlled by the thumb and pointer finger of the surgeon. This permits both sensitivity and maneuverability for the surgeon. The handle is made of a variety of light materials such as aluminum, plastic, or rubber.

At one end of the cannula is a tubing connection which is one of a variety well known to those in the art. A solid connection between the cannula and the flexible tubing is important to avoid liquid leakage during the injecting and aspirating procedures.

The barrel of cannula 14 is made of surgical steel or other suitable material and has a channel or hole extending the length of the barrel. Venting holes at one end of the tube permit the tumescent solution to exit into the patient 15 and for materials to be aspirated from the patient.

FIGS. 2A and 2B are cross sectional views of the headstock of the peristaltic pump and illustrate the reversibility of the pump.

Although this illustration is of a three-ball pump, those of ordinary skill in the art readily recognize that any peristaltic pump could be used in this context.

Other peristaltic pumps have anywhere from two to six balls for the pumping action.

A peristaltic pump's main component is headstock 17 which contains roller mechanism 20 having metal rollers 25A, 25B, and 25C mounted thereon. Roller mechanism 20 is driven by an electric motor. Rollers 25A, 25B, and 25C are enclosed within a cavity of headstock 17 and ride on wall 26.

Tubing 13 extends into the cavity and is positioned between rollers 25A, 25B, and 25C, and wall 26. During rotation of roller mechanism 20, as illustrated by arrow 22A, liquid within tubing 13 is drawn in, as shown by arrow 23A, and then discharged, as shown by arrow 23B. In like manner, rotation as shown by arrow 22B, causes a reverse flow as illustrated by arrows 24A and 24B.

By adjusting the rotational direction of roller mechanism 20, the directional flow is controlled. By controlling the rotational speed of roller mechanism 20, the flow rate is controlled. Hence, by controlling the rotational speed, the injection rate is controlled; and, by controlling the rotational speed during reverse rotation, the aspiration rate is controlled.

Since the surgeon controls the on/off of the peristaltic pump via foot control 16 (of FIG. 1), the peristaltic pump is set for either injection (with rate of flow) or aspiration (with rate of vacuum) by either an assisting surgeon or a surgical nurse as the primary surgeon moves from one stage of the operation to another.

FIG. 3A and FIG. 3B are side and cross sectional views of the preferred cannula used in the present invention.

Cannula 14 consists essentially of barrel or tube portion 30 and handle portion 31. Tube portion 30 has channel 34 therein that extends its length. Access to channel 34 is by way of vents 32. Vents 32 are used to either inject the tumescent solution or aspirate fat/tissue with the tumescent solution.

Handle 31 is preferably small and delicate on the order of less twenty millimeters. Other dimensions for the handle are possible and may be adjusted for the particular surgeon. When the handle is made small, the surgeon is able to delicately manipulate the cannula and obtain enhanced feel and dexterity.

Although the handle may be constructed of a variety of materials such as surgical steel, the preferred material is lighter and is made of such materials as: aluminum, plastic, or rubber. Those of ordinary skill in the art readily recognize a variety of materials which will serve this function.

In the preferred embodiment, connector 33A is affixed to the back of handle 31. Connector 33A permits the affixation of tubing 13 which communicates with channel 34 via a channel through the center of handle 31.

Alternatively, connector 33B is incorporated into the cannula and is used to connect tubing 13 to cannula 14.

FIG. 4A and 4B pictorially show use of the cannula and the resulting delicate grip required from the surgeon.

Cannula 14 is inserted through the patient's skin 42 and into the interior of the patient. Control of cannula 14 is accomplished by a single hand 40 of the surgeon and is usually done by delicately gripping the handle between the thumb and forefinger as shown. This delicate manipulation and control of the cannula 14 is possible, in part, due to the vacuum is being provided by the peristaltic pump.

During the injection of the tumescent solution (FIG. 4A) the peristaltic pump directs the tumescent solution through the tubing 13 as shown by arrow 43. The tumescent solution exits cannula 14 via vents 32 as shown by arrows 41A.

During the aspiration of the fat/tissue (FIG. 4B), the fat/tissue together with some of the tumescent solution is withdrawn via vents 32 as shown by arrows 41B to be collected as illustrated by arrow 43.

Note that for the surgeon, the removal or movement of the cannula when changing from the injection to aspiration procedure is not required. For this change, the peristaltic pump is simply reversed and the cannula serves the aspiration function.

FIGS. 5A, 5B, and 5C pictorially illustrate the injection and aspiration in a patient of the present invention.

Tube 30 of the cannula is inserted into the site having fat 50A and tissue 51. As the tumescent solution is injected to the body (as illustrated in FIG. 5B) via vents 32, as shown by arrows 41A, the solution causes the fat 50B to break apart from each other. The tumescent solution also provides for a local anesthetic as well as a vasoconstrictor (to reduce bleeding during the procedure).

During the aspiration step (FIG. 5C) fat 50C and tissue is drawn through vents 32 as shown by arrows 41B.

In this manner, the cannula is used both to inject the tumescent solution and for the aspiration. Since the tumescent solution and the aspirated material is "liquid", there never is any gap in either the pressure or vacuum during the injection or the aspiration phases. This assures the surgeon of consistent operation of the mechanism.

It is clear from the foregoing that the present invention provides for a vastly improved procedure and mechanism for lipoplastic operations.

What is claimed is:

1. A surgical assembly comprising:
   a) a lipoplastic cannula having an enclosed channel extending therein, a handle portion proximate to a first end thereof, and further having vent openings proximate to an end opposite said handle portion and communicating with said enclosed channel, said handle portion being suitable for use with a single hand of a surgeon and being less than twenty millimeters in diameter;
   b) a flexible bag reservoir containing a medicated liquid being a local anesthetic and a vasoconstrictor;
   c) a flexible clear tubing communicating said channel in said cannula with said flexible bag reservoir; and,
   d) a reversible pump means interposed between said cannula and said flexible bag reservoir for selectively communicating, via said flexible tubing, said medicated liquid from said flexible bag reservoir to said cannula, and for communicating body materials and liquids from a patient via said cannula to said reservoir.

2. The surgical assembly according to claim 1 wherein said cannula includes attachment means for connecting said flexible tubing to said cannula.

3. The surgical assembly according to claim 2 wherein said attachment means is positioned at one end of said cannula in communication with said enclosed channel.

4. The surgical assembly according to claim 1 wherein said reversible pump means is a peristaltic pump having roller means in contact with said flexible tubing for pumping materials within said flexible tubing.

5. The surgical assembly according to claim 4 further including a remote control means, in communication with said peristaltic pump, for engaging said roller means to rotate.

6. The surgical assembly according to claim 5 wherein said remote control means is foot activated.

7. A surgical instrument comprising:
 a) a cannula having a handle portion proximate to a first end thereof and a channel therein, said channel having vent openings proximate to an end opposite said handle portion;
 b) a reservoir containing a sterile liquid;
 c) a flexible tubing communicating said channel in said cannula with said reservoir; and,
 d) a reversible pump means interposed between said cannula and said reservoir for,
  1) selectively communicating, via said flexible tubing, said sterile liquid to said cannula, and,
  2) communicating body materials and liquids from a patient via said cannula to said reservoir.

8. The surgical instrument according to claim 7 wherein the handle of said cannula is less than twenty millimeters in diameter.

9. The surgical instrument according to claim 8 wherein said cannula includes attachment means for connecting said flexible tubing to said cannula.

10. The surgical instrument according to claim 9 wherein said attachment means is positioned at one end of said cannula in communication with said channel.

11. The surgical instrument according to claim 7 wherein said flexible tubing is transparent.

12. The surgical instrument according to claim 7 wherein said reversible pump means is a peristaltic pump having roller means in contact with said flexible tubing for pumping materials within said flexible tubing.

13. The surgical instrument according to claim 12 further including an operator activated control means for directing operation of said roller means.

14. The surgical instrument according to claim 13 wherein said operator activated control means is foot activated.

15. The surgical instrument according to claim 7 wherein said reservoir is a flexible bag and wherein said medicated liquid includes a local anesthetic and a vasoconstrictor.

16. An improved cannula and reservoir assembly for lipoplastic surgery comprising:
 a) a barrel portion having a first end and a second end and having a channel therein and having at least one vent opening proximate to the first end of said barrel, said at least one vent opening being in communication with said channel and for communication of a mixture including a local anesthetic and vasoconstrictor to a site of an operation;
 b) a handle portion positioned at a second end of said barrel;
 c) a reservoir containing a sterile liquid;
 d) a flexible tubing communicating said channel in said barrel portion with said reservoir; and,
 e) a reversible pump means interposed between said barrel portion and said reservoir for selectively communicating, via said flexible tubing, said sterile liquid from said reservoir to said barrel portion, and for communicating body materials and liquids from a patient via said barrel portion to said reservoir.

17. The improved cannula and reservoir assembly according to claim 16 wherein said handle portion is less than twenty millimeters in diameter.

18. The improved cannula and reservoir assembly according to claim 16 wherein said cannula includes attachment means for connecting a flexible tubing to said cannula.

19. The improved cannula and reservoir assembly according to claim 18 wherein said attachment means is positioned at one end of said cannula in communication with said channel.

* * * * *